US012721821B2

(12) United States Patent
Mei et al.

(10) Patent No.: US 12,721,821 B2
(45) Date of Patent: Sep. 1, 2026

(54) PLANT ESSENTIAL OIL AMINO ACID COMPOSITION AND PREPARATION METHOD THEREFOR

(71) Applicant: COCRYSTAL TECHNOLOGY (JIAXING) CO., LTD, Jiaxing (CN)

(72) Inventors: Xuefeng Mei, Shanghai (CN); Fengyuan Wang, Shanghai (CN); Jianrong Wang, Shanghai (CN); Liye Lu, Shanghai (CN); Zaiyong Zhang, Shanghai (CN)

(73) Assignee: COCRYSTAL TECHNOLOGY (JIAXING) CO., LTD., Zhejiang (CN)

( * ) Notice: Subject to any disclaimer, the term of this patent is extended or adjusted under 35 U.S.C. 154(b) by 421 days.

(21) Appl. No.: 18/278,788

(22) PCT Filed: Feb. 24, 2022

(86) PCT No.: PCT/CN2022/077567
§ 371 (c)(1),
(2) Date: Aug. 24, 2023

(87) PCT Pub. No.: WO2022/179539
PCT Pub. Date: Sep. 1, 2022

(65) Prior Publication Data

US 2024/0350427 A1 Oct. 24, 2024

(30) Foreign Application Priority Data

Feb. 24, 2021 (CN) ......................... 202110209829.2

(51) Int. Cl.
*A61K 31/05* (2006.01)
*A61K 9/16* (2006.01)
(Continued)

(52) U.S. Cl.
CPC ............ *A61K 31/05* (2013.01); *A61K 9/1688* (2013.01); *A61K 31/198* (2013.01); *A61K 31/401* (2013.01)

(58) Field of Classification Search
CPC .... A23K 10/30; A23K 20/111; A23K 20/142; A23K 50/30; A23K 50/60; A23K 50/75;
(Continued)

(56) References Cited

U.S. PATENT DOCUMENTS

2005/0118310 A1 6/2005 Lacroix
2020/0306347 A1 10/2020 Rotello et al.

FOREIGN PATENT DOCUMENTS

CN 104161192 A 11/2014
CN 104206822 A 12/2014
(Continued)

OTHER PUBLICATIONS

Mazzeo et al., Designing a Palette of Cocrystals Based on Essential Oil Constituents for Agricultural Applications, ACS Sustainable Chemistry and Engineering, vol. 7, 17929-17940, Sep. 30, 2019 (Year: 2019).*

(Continued)

*Primary Examiner* — Kortney L. Klinkel
*Assistant Examiner* — Padmaja S Rao
(74) *Attorney, Agent, or Firm* — Carter, DeLuca & Farrell LLP

(57) ABSTRACT

The invention relates to a plant essential oil amino acid composition and a preparation method therefor. The composition of the present invention is a composition containing a plant essential oil and amino acids. The composition is obtained by mixing the plant essential oil with amino acids, the plant essential oil being selectively one or two of thymol and carvacrol. The composition of the present invention has a significantly higher melting point and lower volatility, thus (Continued)

significantly improving stability. When being used as an animal growth-promoting feed additive, the composition of the present invention has better palatability and lower death rate.

4 Claims, 5 Drawing Sheets

(51) Int. Cl.
*A61K 31/198* (2006.01)
*A61K 31/401* (2006.01)

(58) Field of Classification Search
CPC ..... A23K 40/10; A23L 33/105; A23L 33/175; A23V 2002/00; A23V 2250/064; A23V 2250/21; A23V 2200/30; A23V 2250/06; A61K 31/401; A61K 31/05; A61K 31/198; A61K 9/1688; A61K 47/183; A61K 8/347; A61K 8/922; A61K 8/44; A61K 2300/00; A61P 31/04; A61Q 19/00
See application file for complete search history.

(56) References Cited

FOREIGN PATENT DOCUMENTS

| | | | | |
|---|---|---|---|---|
| CN | 105832752 | A | 8/2016 | |
| CN | 106344648 | A | 1/2017 | |
| CN | 108033939 | A | 5/2018 | |
| CN | 110269092 | A | 9/2019 | |
| CN | 112189763 | A | 1/2021 | |
| CN | 112998133 | A | 6/2021 | |
| JP | S59-39279 | A | 3/1984 | |
| JP | 2003-183171 | A | 7/2003 | |
| JP | 2010-523551 | A | 7/2010 | |
| JP | 2011-126785 | A | 6/2011 | |
| WO | WO-0069277 | A1 * | 11/2000 | ............. A61P 31/04 |
| WO | 01/90338 | A1 | 11/2001 | |
| WO | 2020/254663 | A2 | 12/2020 | |

OTHER PUBLICATIONS

Teng et al., Amino acid based pharmaceutical cocrystals and hydrate cocrystals of the chlorothiazide: Structural studies and physicochemical properties, Journal of Molecular Structure, vol. 1217, 1-10, May 13, 2020 (Year: 2020).*

Hafeez, A. et al., "Effect of supplementation of phytogenic feed additives (powdered vs. encapsulated) on performance and nutrient digestibility in broiler chickens" Poultry Science (Feb. 2016) pp. 622-629, vol. 95, No. 3, XP009518659.

Du, E. et al., "Effects of thymol and carvacrol supplementation on intestinal integrity and immune responses of broiler chickens challenged with Clostridium perfringens" Journal of Animal Science and Biotechnology (Dec. 2016) pp. 1-10, vol. 7, No. 1, XP055810404.

Koch, M. et al., "The application of metallochromic indicators in colorimetry—I" Talanta (Sep. 1960) pp. 141-146, vol. 5, No. 3-4, XP026566306.

Extended European Search Report issued by the European Patent Office on Jul. 25, 2024 in corresponding EP Patent Application No. 22758903.3.

Notice of Reasons for Refusal issued by the Japanese Patent Office on Aug. 27, 2024 in corresponding JP Patent Application No. 2023-552025, with English translation.

International Search Report issued in corresponding International Application No. PCT/CN2022/077567, dated May 7, 2022, pp. 1-3, English Translation.

Ding et al., "Advances in Edible Essence Microencapsulation", China Condiment, vol. 34, No. 2, Feb. 28, 2009. (1 page). Abstract only.

He at al., "Zwitterionic Cocrystals of Flavonoids and Proline: Solid-State Characterization, Pharmaceutical Properties, and Pharmacokinetic Performance", Crystal Growth Design, vol. 16, Mar. 9, 2016 (22 pages).

Wang et al., "Machine-Learning-Guided Cocrystal Prediction Based on Large Data Base", Crystal Growth Design, vol. 20, Mar. 9, 2016 (34 pages).

* cited by examiner

PLANT ESSENTIAL OIL AMINO ACID COMPOSITION AND PREPARATION METHOD THEREFOR

CROSS REFERENCE TO RELATED APPLICATIONS

The present application is a national stage application of International Application No. PCT/CN2022/077567, filed Feb. 24, 2022, which claims the benefit of and priority to Chinese Patent Application No. 202110209829.2, filed Feb. 24, 2021, the entire contents of each of which are hereby incorporated by reference herein in their entirety.

TECHNICAL FIELD

The invention relates to the technical field of plant essential oil alternatives to antibiotics, in particular to a composition of a plant essential oil and an amino acid, which has improved stability of plant essential oil and reduced volatilization, and a method for preparing the same. The composition has more excellent thermal stability.

BACKGROUND ART

Since 2006, the European Union has completely banned the use of growth-promoting antibiotics feed additives in livestock and poultry feed. The current animal health, growth, and reproductive performance are very good. The current use of antibiotics in the breeding process in the EU has been greatly reduced, only up to 70% of the amount used in 2006, that is, the use of antibiotics for treatment has been reduced by 30%. While the health of the animals has been significantly improved, showing remarkable achievements. The United States has strictly restricted the use of "antibiotics of medical importance to humans" in animal production since Jan. 1, 2017. China has issued a number of "anti-antibiotics" regulations and policies since 2015, and the use of a total of 8 kinds of antibacterial drugs such as lomefloxacin, colistin sulfate and olaquindox in animal feed or animal breeding process has been successively banned. And the use of growth-promoting antibiotics feed additives in feed were completely banned in 2020. Once feed antibiotics are banned, the antibacterial components of herbal plants for thousands of years, such as carvacrol and thymol components in oregano oil, vanilla oil and sweet oregano oil undoubtedly become the first choice of antibacterial agents. Carvacrol and thymol have strong bactericidal ability with a minimum inhibitory concentration (MIC) of only 0.12-50 ppm, and can improve the immunity of animals. Carvacrol and thymol have a unique bactericidal mechanism which prevents bacteria from developing resistance, and can be artificially synthesized in large quantities.

Thymol and carvacrol have antibacterial, antiseptic and antioxidative effects, and are widely used in oral hygiene and food additives. The chemical structure of thymol is shown in formula I, and that of carvacrol is shown in formula II.

I

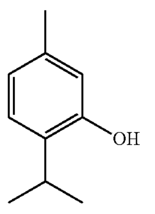

-continued

II

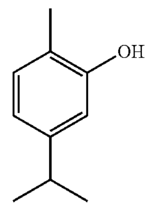

Both thymol and carvacrol belong to plant essential oils and are the main components (60-80%) of oregano oil extract. Because thymol and carvacrol have synergistic antibacterial and bactericidal activities, they are rarely used alone and are the main active ingredients in commercially available essential oil alternatives to antibiotics. However, thymol and carvacrol have low melting points (50° C. for thymol; 2° C. for carvacrol). So they are thermally unstable and volatile during production, storage, transportation and granulation as feed additives, resulting in a large loss of active ingredients. A variety of methods have been developed to improve the stability of thymol and carvacrol during long-term storage and high-temperature granulation processing. For example, CN101331915A discloses that thymol and eugenol are directly mixed with benzoic acid; CN103478232A discloses an inclusion compound of carvacrol and β-cyclodextrin, achieving a sustained release effect; and CN107753462A discloses that a polymer material matrix is used to protect thymol and carvacrol. However, none of the above-mentioned prior art can significantly improve the stability of thymol and carvacrol during long-term storage and high-temperature granulation processing.

Therefore, it is necessary to develop new technologies that can solve the chemical stability problem of plant essential oils.

SUMMARY OF THE INVENTION

Therefore, the present invention aims at the above-mentioned deficiencies in the essential oil alternatives to antibiotics, and it is unexpectedly found during the research and development of a product with high stability and low volatility that after sarcosine or proline is used to interact with thymol or carvacrol to form a composition, the melting point and stability of the composition are greatly improved. The present invention obtains a composition by adding an amino acid as a specific auxiliary compound, and the auxiliary compound has non-covalent bond interaction with thymol or carvacrol at the molecular level. At the same time, the combined use of thymol and carvacrol shows significant synergistic effects of antibacterial, bactericidal and antioxidant. Carvacrol as a liquid state at room temperature, the prepared stable composition solid powder is more convenient to be applied in the fields of food additives, pharmaceutical additives and feed additives. It is found from the research of the present invention that the composition formed from thymol and carvacrol has significantly improved melting point (for example, the melting point is 123° C. for the composition of thymol and L-proline at a molar ratio of 1:1, 133° C. for the composition of carvacrol and L-proline at a molar ratio of 1:1), improving the thermal stability. In addition, the preparation method of the composition is simple with good reproducibility, thus being beneficial to the improvement of process treatment and physical and chemical properties.

Therefore, the present invention provides a composition that improves the stability of plant essential oils and reduces volatilization, that is, a composition of a plant essential oil and an amino acid, the plant essential oil may be thymol and/or carvacrol, and the amino acid may be sarcosine and/or proline. The composition of the invention can remarkably increase the melting point of the plant essential oil, reduce the volatility, and thereby remarkably improve the stability. When the composition of the invention is used as an animal growth-promoting feed additive, it has better palatability and lower death rate.

The first object of the present invention is to provide a composition comprising a plant essential oil and an amino acid.

The second object of the present invention is to provide a method for preparing the composition comprising a plant essential oil and an amino acid.

The third object of the present invention is to provide a product comprising the composition of a plant essential oil and an amino acid.

The fourth object of the present invention is to provide an application of the composition comprising a plant essential oil and an amino acid in preparation of a health product, a food, a cosmetic, a medicine, a pharmaceutical excipient or a feed.

According to the first aspect of the present invention, there is provided a composition comprising a plant essential oil and an amino acid, said composition is obtained by mixing a plant essential oil with an amino acid, said plant essential oil is one or two selected from the group consisting of thymol and carvacrol, and the amino acid is one or two selected from the group consisting of L-proline and sarcosine.

Preferably, the plant essential oil and the amino acid are mixed at a molar ratio of 9-1:1-9, preferably 2-1:1-2. For example, the molar ratio may be 1:9, 1:2, 1:1, 2:1, 9:1, etc., but the present invention is not limited thereto.

Preferably, the plant essential oil is a mixture of thymol and carvacrol, wherein the molar ratio of thymol and carvacrol may be 9-1:1-9, preferably 2-1:1-2.

In an embodiment, the composition of the present invention is obtained by mixing thymol with sarcosine at a molar ratio of 1:2.

In an embodiment, the composition of the present invention is obtained by mixing thymol with L-proline at a molar ratio of 1:1.

In an embodiment, the composition of the present invention is obtained by mixing carvacrol with L-proline at a molar ratio of 1:1.

In an embodiment, the composition of the present invention is obtained by mixing carvacrol with L-proline at a molar ratio of 2:1.

In an embodiment, the composition of the present invention is obtained by mixing thymol, carvacrol and L-proline at a molar ratio of 1:1:2.

In an embodiment, the composition of the present invention is obtained by mixing thymol, carvacrol and sarcosine at a molar ratio of 1:1:2.

In an embodiment, the composition of the present invention is obtained by mixing thymol with sarcosine at a molar ratio of 2:1.

In an embodiment, the composition of the present invention is obtained by mixing thymol with L-proline at a molar ratio of 1:2.

In an embodiment, the composition of the present invention is obtained by mixing carvacrol with L-proline in a molar ratio of 1:2.

In an embodiment, the composition of the present invention is obtained by mixing thymol with sarcosine at a molar ratio of 2:1.

In an embodiment, the composition of the present invention is obtained by mixing thymol with sarcosine at a molar ratio of 1:3.

In an embodiment, the composition of the present invention is obtained by mixing carvacrol with sarcosine at a molar ratio of 1:2.

In an embodiment, the composition of the present invention is obtained by mixing thymol with sarcosine at a molar ratio of 1:9.

In an embodiment, the composition of the present invention is obtained by mixing thymol with sarcosine at a molar ratio of 9:1.

In an embodiment, the composition of the present invention is obtained by mixing thymol with L-proline at a molar ratio of 1:9.

In an embodiment, the composition of the present invention is obtained by mixing thymol and L-proline at a molar ratio of 9:1.

In an embodiment, the composition of the present invention is obtained by mixing carvacrol with L-proline in a molar ratio of 1:9.

In an embodiment, the composition of the present invention is obtained by mixing thymol, carvacrol and L-proline at a molar ratio of 1:1:18.

In the composition of the present invention, preferably, the mixing is realized by one of the following methods (1) and (2):

Method (1): the plant essential oil and the amino acid are recrystallized in a solvent to obtain a white precipitate, and the precipitate is dried to obtain a composition of the present invention;

Method (2): the plant essential oil and the amino acid are mixed, added to a crushing equipment to make them fully contact by mechanical force, or a solution of the mixture is subjected to spray-drying, or the mixture is treated with an extruder, and after partial or complete reaction, a composition comprising the plant essential oil and the amino acid is obtained.

In the composition of the present invention, in the above method (1), the solvent includes all solvents that have certain solubility to the raw materials and do not cause deterioration of the raw materials, preferably the solvent is one or more selected from the group consisting of water, an alcohol, a ketone, an ester, an alkane, an aromatic hydrocarbon and a halogenated alkane; more preferably, the solvent is one or more selected from the group consisting of methanol, ethanol, ethyl acetate, acetone, and methylene chloride.

In the composition of the present invention, in the above method (2), the crushing equipment is selected from the group consisting of a ball mill, a pulverizer, a mixer and a stirring device.

The above methods (1) and (2) are simple to operate. It is easy to control the crystallization process, the crystallinity is high, the reproducibility is good, and the composition comprising thymol and/or carvacrol and amino acid can be stably obtained.

In a preferred embodiment of the present invention, the composition comprising a plant essential oil and an amino acid is obtained by mixing thymol with sarcosine at a molar ratio of 1:2. Preferably, the composition has an X-ray powder diffraction pattern showing characteristic peaks at 2θ angles of about 6.4°±0.2°, 12.1°±0.2°, 12.4°±0.2°, 17.7°±0.2°, 20.2°±0.2°, 22.1°±0.2°, 23.0°±0.2°, 23.7°±0.2° and 25.1°±0.2°. More preferably, the composition has an X-ray powder diffraction pattern substantially as shown in FIG. 1. Preferably, the composition has a differential scanning calorimetry pattern showing a characteristic endothermic peak at about 129±2° C.; and more preferably, it has a differential scanning calorimetry pattern substantially as shown in FIG. 2.

In a preferred embodiment of the present invention, the composition comprising a plant essential oil and an amino acid is obtained by mixing thymol with L-proline at a molar ratio of 1:1. Preferably, the composition has an X-ray powder diffraction pattern showing characteristic peaks at 2θ angles of about 6.2°±0.2°, 6.9°±0.2°, 12.5°±0.2°, 13.8°±0.2°, 18.0°±0.2°, 18.4°±0.2°, 18.7°±0.2°, 19.1°±0.2°, 19.3°±0.2°, 21.1°±0.2° and 24.8°±0.2°. More preferably, the composition has an X-ray powder diffraction substantially as shown in FIG. 3. Preferably, the composition has a differential scanning calorimetry pattern showing a characteristic endothermic peak at about 123±2° C.; and more preferably, it has a differential scanning calorimetry pattern substantially as shown in FIG. 4.

In a preferred embodiment of the present invention, the composition comprising a plant essential oil and an amino acid is obtained by mixing carvacrol with L-proline at molar ratio of 1:1. Preferably, the composition has an X-ray powder diffraction pattern showing characteristic peaks at 2θ angles of about 6.9°±0.2°, 11.5°±0.2°, 13.6°±0.2°, 13.9°±0.2°, 19.0°±0.2°, 19.2°±0.2°, 23.1°±0.2° and 24.9°±0.2°. More preferably, the composition has an X-ray powder diffraction pattern substantially as shown in FIG. 5. Preferably, the composition has a differential scanning calorimetry pattern showing a characteristic endothermic peak at about 133±2° C.; and more preferably, it has a differential scanning calorimetry pattern substantially as shown in FIG. 6.

In a preferred embodiment of the present invention, the composition comprising a plant essential oil and an amino acid is obtained by mixing carvacrol with L-proline at a molar ratio of 2:1. Preferably, the composition has an X-ray powder diffraction pattern showing characteristic peaks at 2θ angles of about 6.5°±0.2°, 11.0°±0.2°, 13.1°±0.2°, 13.2°±0.2°, 15.0°±0.2°, 15.5°±0.2°, 15.8°±0.2°, 17.5°±0.2°, 19.7°±0.2°, 20.5°±0.2°, 21.6°±0.2°, 21.90±0.20, 23.6°±0.2°, 25.1°±0.2° and 26.7°±0.2°. More preferably, the composition has an X-ray powder diffraction pattern substantially as shown in FIG. 7. Preferably, the composition has a differential scanning calorimetry pattern showing a characteristic endothermic peak at about 80±2° C.; and more preferably, it has a differential scanning calorimetry pattern substantially as shown in FIG. 8.

In a preferred embodiment of the present invention, the composition comprising a plant essential oil and an amino acid is obtained by mixing thymol, carvacrol and L-proline at a molar ratio of 1:1:2. Preferably, the composition has an X-ray powder diffraction pattern showing characteristic peaks at 2θ angles of about 6.2°±0.2°, 6.8°±0.2°, 12.5°±0.2°, 13.8°±0.2°, 18.4°±0.2°, 18.8°±0.2°, 19.4°±0.2°, 21.3°±0.2°, 24.8°±0.2° and 25.0°±0.2°. More preferably, the composition has an X-ray powder diffraction pattern substantially as shown in FIG. 9. Preferably, the composition has a differential scanning calorimetry pattern showing a characteristic endothermic peak at about 125±2° C.; and more preferably, it has a differential scanning calorimetry pattern substantially as shown in FIG. 10.

By comparison, it can be found that the X-ray powder diffraction pattern of the composition obtained by mixing thymol, carvacrol and L-proline at a molar ratio of 1:1:2 is basically a superposition of the X-ray powder diffraction patterns of the composition obtained by mixing thymol with L-proline at a molar ratio of 1:1 and the composition obtained by mixing carvacrol with L-proline at a molar ratio of 1:1, while the differential scanning calorimetry pattern is affected by components other than the composition, and its characteristic endothermic peak is changed compared with the characteristic endothermic peaks of the corresponding compositions.

The second aspect of the present invention provides a method for preparing a composition comprising a plant essential oil and an amino acid, comprising: a step of mixing the plant essential oil with the amino acid to obtain the composition comprising the plant essential oil and the amino acid.

In the preparation method of the present invention, preferably, the amino acid is one or two selected from the group consisting of L-proline and sarcosine.

In the preparation method of the present invention, preferably, the plant essential oil and the amino acid are mixed at a molar ratio of 9-1:1-9, preferably 2-1:1-2. For example, the molar ratio may be 1:9, 1:2, 1:1, 2:1, 9:1, etc., but the present invention is not limited thereto.

In the preparation method of the present invention, preferably, in the plant essential oil, the molar ratio of thymol and carvacrol may be 9-1:1-9, preferably 2-1:1-2.

In an embodiment, the preparation method of the present invention comprises the step of mixing thymol with sarcosine at a molar ratio of 1:2 to obtain the composition.

In an embodiment, the preparation method of the present invention comprises the step of mixing thymol with L-proline at a molar ratio of 1:1 to obtain the composition.

In an embodiment, the preparation method of the present invention comprises the step of mixing carvacrol with L-proline at a molar ratio of 1:1 to obtain the composition.

In an embodiment, the preparation method of the present invention comprises the step of mixing carvacrol with L-proline at a molar ratio of 2:1 to obtain the composition.

In an embodiment, the preparation method of the present invention comprises the step of mixing thymol, carvacrol and L-proline at a molar ratio of 1:1:2 to obtain the composition.

In an embodiment, the preparation method of the present invention comprises the step of mixing thymol, carvacrol and sarcosine at a molar ratio of 1:1:2 to obtain the composition.

In an embodiment, the preparation method of the present invention comprises the step of mixing thymol with sarcosine at a molar ratio of 2:1 to obtain the composition.

In an embodiment, the preparation method of the present invention comprises the step of mixing thymol with sarcosine at a molar ratio of 1:3 to obtain the composition.

In an embodiment, the preparation method of the present invention comprises the step of mixing thymol with L-proline at a molar ratio of 1:2 to obtain the composition.

In an embodiment, the preparation method of the present invention comprises the step of mixing carvacrol with L-proline in a molar ratio of 1:2 to obtain the composition.

In an embodiment, the preparation method of the present invention comprises the step of mixing thymol with sarcosine at a molar ratio of 2:1 to obtain the composition.

In an embodiment, the preparation method of the present invention comprises the step of mixing carvacrol with sarcosine at a molar ratio of 1:2 to obtain the composition.

In an embodiment, the preparation method of the present invention comprises the step of mixing thymol with sarcosine at a molar ratio of 1:9 to obtain the composition.

In an embodiment, the preparation method of the present invention comprises the step of mixing thymol with sarcosine at a molar ratio of 9:1 to obtain the composition.

In an embodiment, the preparation method of the present invention comprises the step of mixing thymol with L-proline at a molar ratio of 1:9 to obtain the composition.

In an embodiment, the preparation method of the present invention comprises the step of mixing thymol and L-proline at a molar ratio of 9:1 to obtain the composition.

In an embodiment, the preparation method of the present invention comprises the step of mixing carvacrol with L-proline in a molar ratio of 1:9 to obtain the composition.

In an embodiment, the preparation method of the present invention comprises the step of mixing thymol, carvacrol and L-proline at a molar ratio of 1:1:18 to obtain the composition.

In the preparation method of the present invention, preferably, the mixing is realized by one of the following methods (1) and (2):

Method (1): the plant essential oil and the amino acid are recrystallized in a solvent to obtain a precipitate, and the precipitate is dried to obtain a composition comprising the plant essential oil and the amino acid;

Method (2): the plant essential oil and the amino acid are mixed, added to a crushing equipment to make them fully contact by mechanical force, or a solution of the mixture is subjected to spray-drying, or the mixture is treated with an extruder, and after partial or complete reaction, a composition comprising the plant essential oil and the amino acid is obtained.

In the preparation method of the present invention, in the above method (1), the solvent includes all solvents that have certain solubility to the raw materials and do not cause deterioration of the raw materials, preferably the solvent is one or more selected from the group consisting of water, an alcohol, a ketone, an ester, an alkane, an aromatic hydrocarbon and a halogenated alkane. More preferably, the solvent is one or more selected from the group consisting of methanol, ethanol, ethyl acetate, acetone, and methylene chloride.

In the preparation method of the present invention, in the above method (2), the crushing equipment is selected from the group consisting of a ball mill, a pulverizer, a mixer and a stirring device.

In an embodiment, the plant essential oil and the amino acid are added to a ball mill and vibrated at a vibrating frequency of 5-60 Hz, preferably 30 Hz, for a vibrating time of 5-60 minutes, preferably 20 minutes, to obtain the composition of the present invention.

In an embodiment, the plant essential oil and the amino acid are added into a pulverizer for a pulverizing time of 1-60 minutes, preferably 2 minutes, to obtain the composition of the present invention.

In the preparation method of the present invention, the above method (1) and method (2) are simple to operate. It is easy to control the crystallization process, the crystallinity is high, and the reproducibility is good, and the composition comprising thymol and/or carvacrol and the amino acid can be stably obtained.

The third aspect of the present invention provides a product, such as a health care product, a food, a cosmetic, a medicine, a pharmaceutical excipient or a feed, which comprises the above-mentioned composition of the plant essential oil and the amino acid.

Other suitable raw materials required by the product can also be included in the product. For example, the food can include food main ingredients and edible food additives acceptable in food, such as a sweetener, a flavoring agent, a preservative, a fragrance, a colorant, etc.; the cosmetic may contain a cosmetic main ingredient and an additive that are cosmetically acceptable, such as a solvent, a fragrance, a preservative, a perfume, a colorant, etc.; the medicine may contain a pharmaceutically active ingredient and a pharmaceutically acceptable excipient, such as a carrier, a diluent, a adjuvant, a colorant, etc.; the feed can contain a feed main ingredient, such as a soybean meal, hay, etc., and an acceptable feed auxiliary material in the feed, such as a sweetener, a flavoring agent, a preservative, a fragrance, a colorant, etc., but the present invention is not limited thereto.

The above product is prepared by adding the composition comprising the plant essential oil and the amino acid according to the present invention. Except for adding the composition comprising the plant essential oil and the amino acid of the present invention, the preparation method of the product can be prepared according to its conventional method.

The various ratios mentioned herein are all molar ratios; the used term feed means any compound, preparation, mixture or composition suitable for or intended to be taken by animals. The auxiliary compound described herein interacts with part or all of the main molecules at the molecular level. The thymol and carvacrol described herein are applicable to natural and synthetic sources.

The present invention has been described in detail above, but the above-described embodiments are merely illustrative in nature and are not intended to limit the present invention. Furthermore, the present invention is not to be bound by any theory presented in the preceding prior art or summary of the invention, or the following examples.

Unless expressly stated otherwise, throughout this specification, numerical ranges include any subranges therein and any numerical value in the increments by the smallest subunit of a given value therein. Unless expressly stated otherwise, throughout this specification numerical values represent approximate measures or limitations of ranges that include minor deviations from the given values and embodiments having about the stated value as well as having the exact value stated. Except in the working examples provided at the end of the detailed description, all numerical values of parameters (e.g., amounts or conditions) in this specification (including the appended claims) should in all cases be understood to be understood by the term "about" modifier, regardless of whether "about" actually precedes the numerical value. "About" indicates that the stated value allows for some imprecision (some close to exactness in the value; about or reasonably close to the value; approximation). If the imprecision provided by "about" is not understood in the art with this ordinary meaning, then "about" as used herein at least indicates the variation that can be produced by ordinary methods of measuring and using these parameters. For example, "about" may include variations of 10% or less, 5% or less, 4% or less, 3% or less, 2% or less, 1% or less, or 0.5% or less, and in some respects, a variation of 0.1% or less.

Unless expressly stated otherwise, the terms "comprising", "including", "having", "containing" or any other similar terms throughout the application documents are open-ended terms, which mean that in addition to these elements listed herein, other elements which are not specifically listed but are generally inherent in a composition or article may be included in the composition or article. In addition, the interpretation of the terms "comprising", "including", "having" and "containing" used herein should be deemed to specifically disclose and also cover closed or semi-closed conjunctions such as "consisting of" and "consisting essentially of". "Consisting essentially of" means that the elements listed herein make up more than 95%, more than 97%, or in some aspects, more than 99% of the composition or article.

Beneficial Effect

The present invention provides a composition in which thymol and/or carvacrol as a phenolic main active ingredient is combined with an amino acid by interaction at the molecular level, in order to solve the problem of poor stability and easy volatilization loss during the use of essential oil products. Compared with the perfume itself, the melting points of the compositions 1-4 of the present invention are increased by 79, 73, 131 and 78° C., respectively. The mechanism of the composition of the present invention is that the melting points of thymol and carvacrol are increased, the vapor pressures thereof are significantly reduced, thereby reducing volatilization and improving the stability of spices during storage and processing. Taking the composition 5 as an example, it shows more excellent stability than commercially available products during storage and granulation processing (Test Example 4 and Test Example 5). At the same time, the advantages of using the compositions provided by the present invention as an animal feed additives are that the compositions provided by the present invention are less volatile, have better palatability and improved stability, and fully exert antibacterial properties in animals and reduce the death rate while maintaining quality and quantity. It can be shown from the test results in meat ducks that the composition provided by the present invention has the effect of significantly reducing the death rate.

MODE OF THE INVENTION

The present invention will be further described below in conjunction with specific examples, but the present invention is not limited by the specific examples.

The experimental methods used in the following examples were conventional methods unless otherwise specified.

The materials and reagents used in the following examples could be obtained from commercial sources unless otherwise specified.

Thymol and carvacrol were purchased from Nanjing Jiulonghui Spices Co., Ltd.; sarcosine and L-proline were purchased from Sinopharm Chemical Reagent Co., Ltd.

The ball mill was purchased from Shanghai Jingxin Industrial Development Co., Ltd.

The pulverizer was purchased from Xinlongwei Machinery Parts Co., Ltd.

Detection Instrument and Analysis Method:

For X-ray powder diffraction (XRPD) method, instrument model: Bruker D8 advance, target: Cu Kα (40 kV, 40 mA), the standard sample that comes with the instrument was used to correct the peak position of the instrument before use. The acquisition software is Diffrac Plus XRD Commander, and the analysis software is MDI Jade 6.0. The samples were tested at room temperature, and the samples to be tested were placed on an organic glass slide. Distance from sample to detector: 30 cm, scanning range: 3-40° (2θ value), scanning step: 0.02°, step length: 0.1 seconds/step.

For differential scanning calorimetry (DSC) method, instrument model: TA DSC Q2000, temperature range: 50-200° C., scan rate: 10° C./min, nitrogen flow rate: 50 mL/min.

For thermogravimetric analysis (TGA) method, instrument model: Netzsch TG 209F3 thermogravimetric analyzer detection, temperature: 80° C. for 100 minutes, purge gas: 25 mL/min.

The industry standard NY/T 3137-2017 of the Ministry of Agriculture was adopted as the content analysis method for thymol and carvacrol.

PREPARATION EXAMPLE

Preparation Example 1: Preparation of Composition 1

The preparation process of Composition 1 was as follows. 5 mmol of thymol and 10 mmol of sarcosine were added at a molar ratio of 1:2 to 20 mL of methanol. The mixture was stirred at 60° C. for 1 h, and then recrystallized to obtain a white precipitate. The precipitate was filtered and put in a vacuum drying oven to be dried at room temperature to obtain Composition 1 formed by thymol and sarcosine, with a yield of 86%.

Alternatively, 5 mmol of thymol and 10 mmol of sarcosine were added to a ball mill at a molar ratio of 1:2 and vibrated at a vibrating frequency of 30 Hz for a vibrating time of 20 minutes to obtain Composition 1 formed by thymol and sarcosine, which was a crystalline powder with good fluidity, with a yield of 98%.

Alternatively, 1 mol of thymol and 2 mol of sarcosine were added to a pulverizer at a molar ratio of 1:2 and pulverized for 2 minutes to obtain Composition 1 formed by thymol and sarcosine, which was a crystalline powder with good fluidity, with a yield of 95%.

Figure 1:
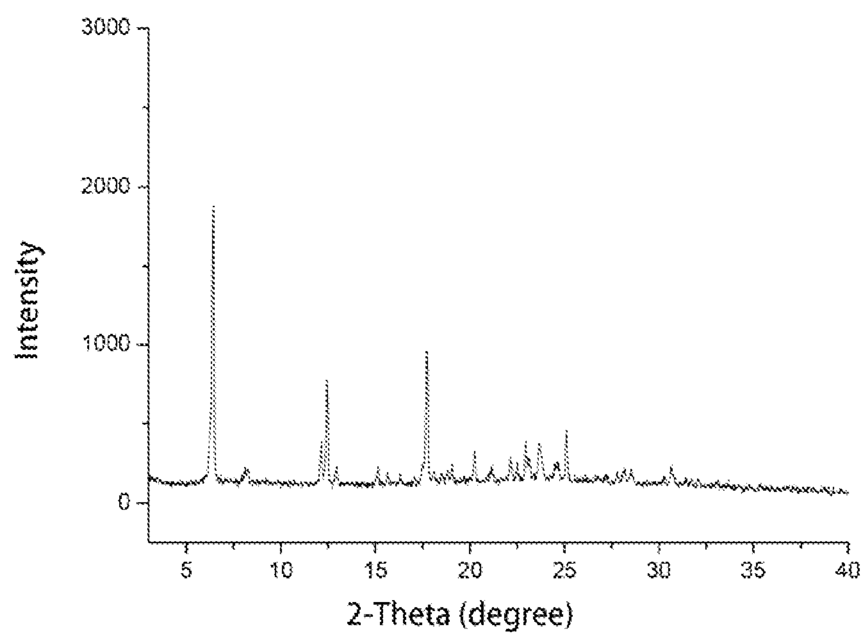
FIG. 1 is the X-ray powder diffraction (XRPD) pattern of Composition 1.
Figure 2:
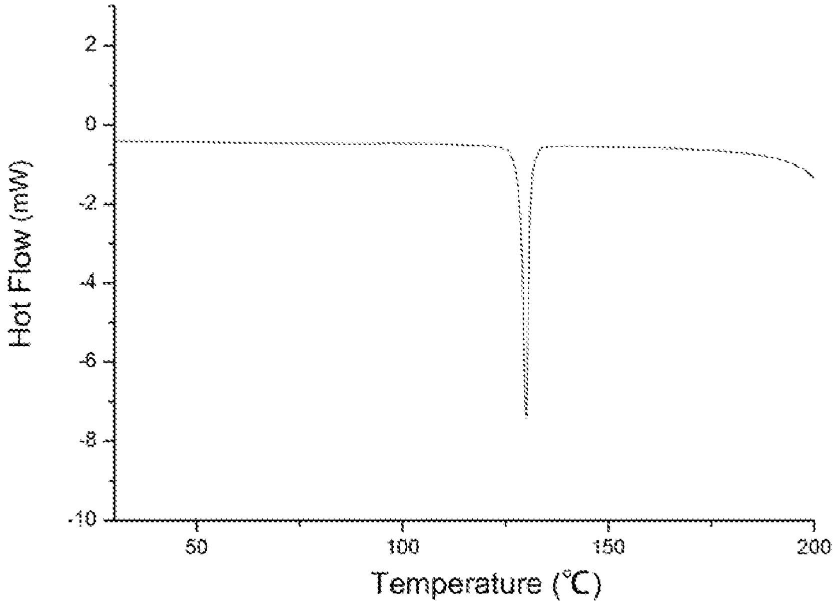
FIG. 2 is the differential scanning calorimetry (DSC) pattern of Composition 1.

The samples prepared in Preparation Example 1 were characterized by X-ray powder diffraction (XRPD) and differential scanning calorimetry (DSC) methods. The results of the samples obtained in the above three preparation processes were consistent, as shown in FIGS. 1 and 2. FIG. 1 is the X-ray powder diffraction (XRPD) pattern of Composition 1; and FIG. 2 is the differential scanning calorimetry (DSC) pattern of Composition 1.

Preparation Example 2: Preparation of Composition 2

The preparation process of Composition 2 was as follows.

10 mmol of thymol and 10 mmol of L-proline were added at a molar ratio of 1:1 to 10 mL of ethanol. The mixture was stirred at 40° C. for 1 h, and then recrystallized to obtain a white precipitate. The precipitate was filtered and put in a vacuum drying oven to be dried at room temperature to obtain Composition 2 formed by thymol and L-proline, with a yield of 92%.

Alternatively, 10 mmol of thymol and 10 mmol of L-proline were added to a ball mill at a molar ratio of 1:1 and vibrated at a vibrating frequency of 30 Hz for a vibrating time of 20 minutes to obtain Composition 2 formed by thymol and L-proline, which was a crystalline powder with good fluidity, with a yield of 98%.

Alternatively, 1 mol of thymol and 1 mol of L-proline were added to a pulverizer at a molar ratio of 1:1 and pulverized for 2 minutes to obtain Composition 2 formed by thymol and L-proline, which was a crystalline powder with good fluidity, with a yield of 94%.

Figure 3:
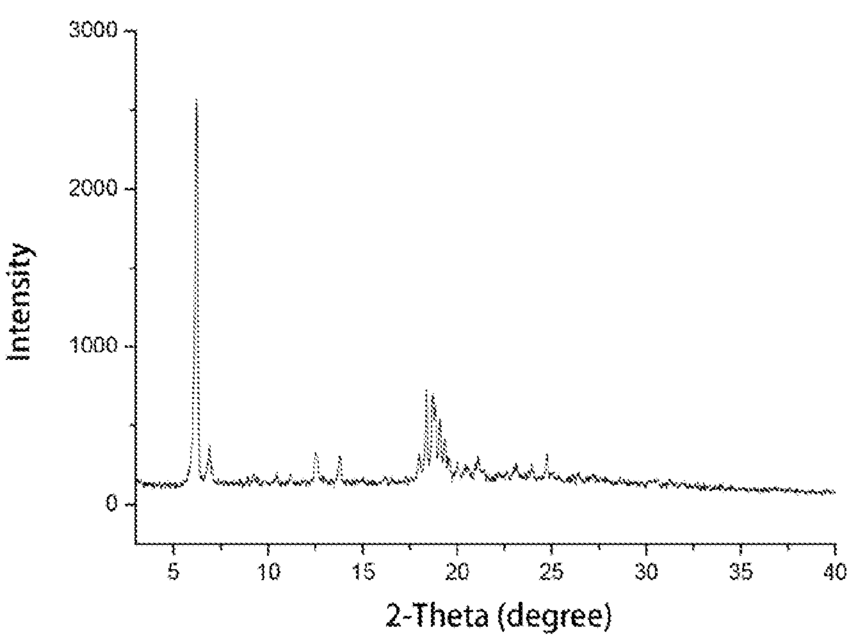
FIG. 3 is the X-ray powder diffraction (XRPD) pattern of Composition 2.
Figure 4:
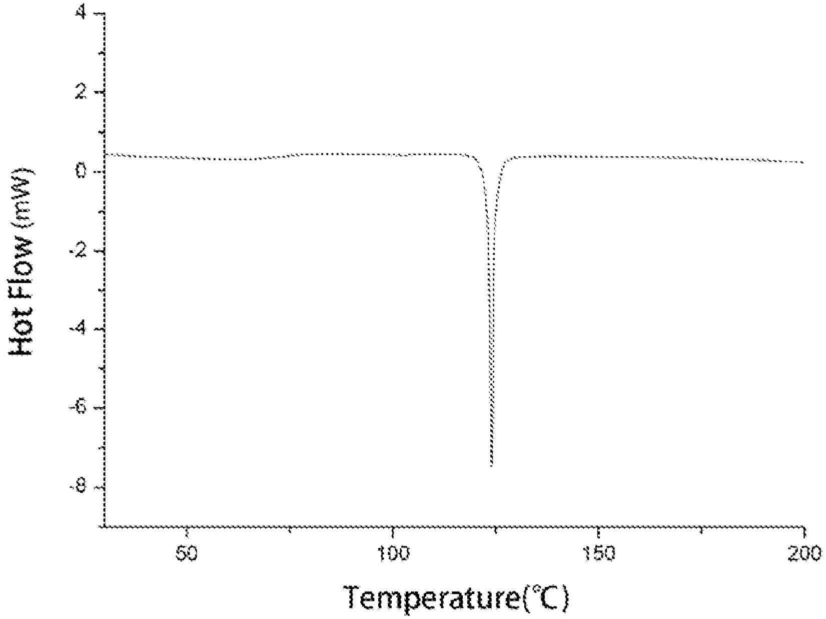
FIG. 4 is the differential scanning calorimetry (DSC) pattern of Composition 2.

The samples prepared in Preparation Example 2 were characterized by X-ray powder diffraction (XRPD) and differential scanning calorimetry (DSC) methods. The results of the samples obtained in the above three preparation processes were consistent, as shown in FIGS. 3 and 4. FIG. 3 is the X-ray powder diffraction (XRPD) pattern of Composition 2; and FIG. 4 is the differential scanning calorimetry (DSC) pattern of Composition 2.

Preparation Example 3: Preparation of Composition 3

The preparation process of Composition 3 was as follows.

10 mmol of carvacrol and 10 mmol of L-proline were added at a molar ratio of 1:1 to 10 mL of ethanol. The mixture was stirred at 40° C. for 1 h, and then recrystallized to obtain a white precipitate. The precipitate was filtered and put in a vacuum drying oven to be dried at room temperature to obtain Composition 3 formed by carvacrol and L-proline, with a yield of 94%.

Alternatively, 10 mmol of carvacrol and 10 mmol of L-proline were added to a ball mill at a molar ratio of 1:1 and vibrated at a vibrating frequency of 30 Hz for a vibrating time of 20 minutes to obtain Composition 3 formed by carvacrol and L-proline, which was a crystalline powder with good fluidity, with a yield of 98%.

Alternatively, 10 mol of carvacrol and 10 mol of L-proline were added to a pulverizer at a molar ratio of 1:1 and pulverized for 2 minutes to obtain Composition 3 formed by carvacrol and L-proline, which was a crystalline powder with good fluidity, with a yield of 94%.

Figure 5:
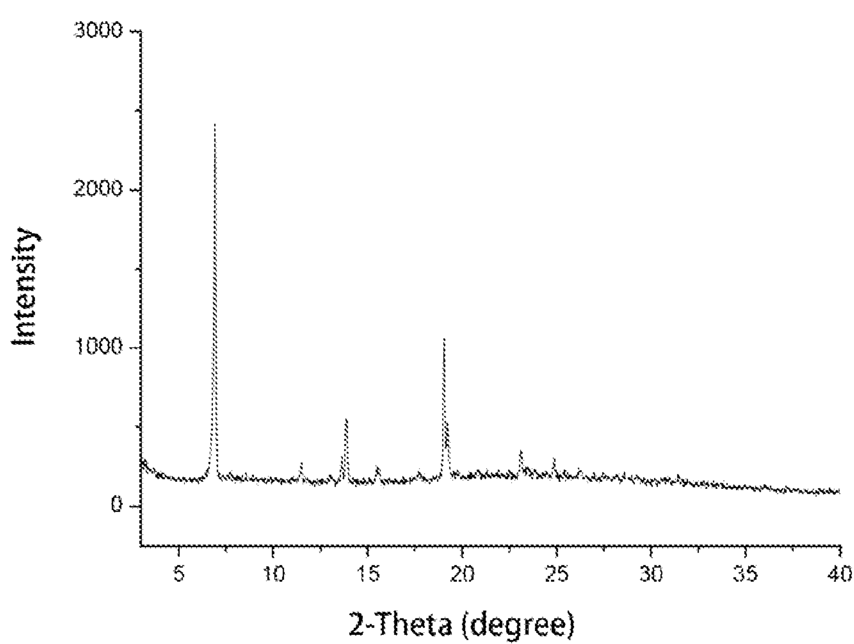
FIG. 5 is the X-ray powder diffraction (XRPD) FIG. of Composition 3.
Figure 6:
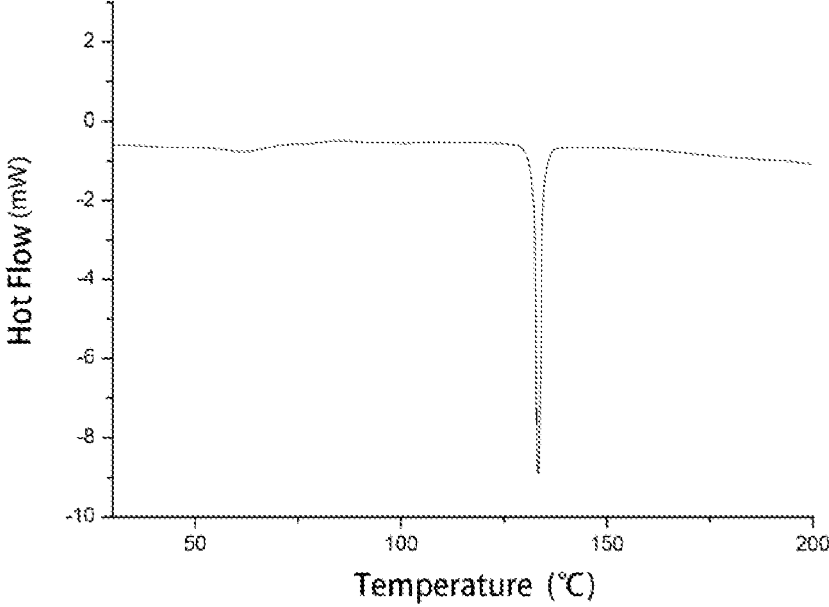
FIG. 6 is the differential scanning calorimetry (DSC) pattern of Composition 3.

The samples prepared in Preparation Example 3 were characterized by X-ray powder diffraction (XRPD) and differential scanning calorimetry (DSC) methods. The results of the samples obtained in the above three preparation processes were consistent, as shown in FIGS. 5 and 6. FIG. 5 is the X-ray powder diffraction (XRPD) pattern of Composition 3; and FIG. 6 is the differential scanning calorimetry (DSC) pattern of Composition 3.

Preparation Example 4: Preparation of Composition 4

The preparation process of Composition 4 was as follows.

10 mmol of carvacrol and 5 mmol of L-proline were added at a molar ratio of 2:1 to 10 mL of ethanol. The mixture was stirred at 40° C. for 1 h, and then recrystallized to obtain a white precipitate. The precipitate was filtered and put in a vacuum drying oven to be dried at room temperature to obtain Composition 4 formed by carvacrol and L-proline, with a yield of 82%.

Alternatively, 10 mmol of carvacrol and 5 mmol of L-proline were added to a ball mill at a molar ratio of 2:1 and vibrated at a vibrating frequency of 30 Hz for a vibrating time of 20 minutes to obtain Composition 4 formed by carvacrol and L-proline, which was a crystalline powder with good fluidity, with a yield of 98%.

Alternatively, 10 mol of carvacrol and 5 mol of L-proline were added to a pulverizer at a molar ratio of 2:1 and pulverized for 2 minutes to obtain Composition 4 formed by carvacrol and L-proline, which was a crystalline powder with good fluidity, with a yield of 96%.

Figure 7:
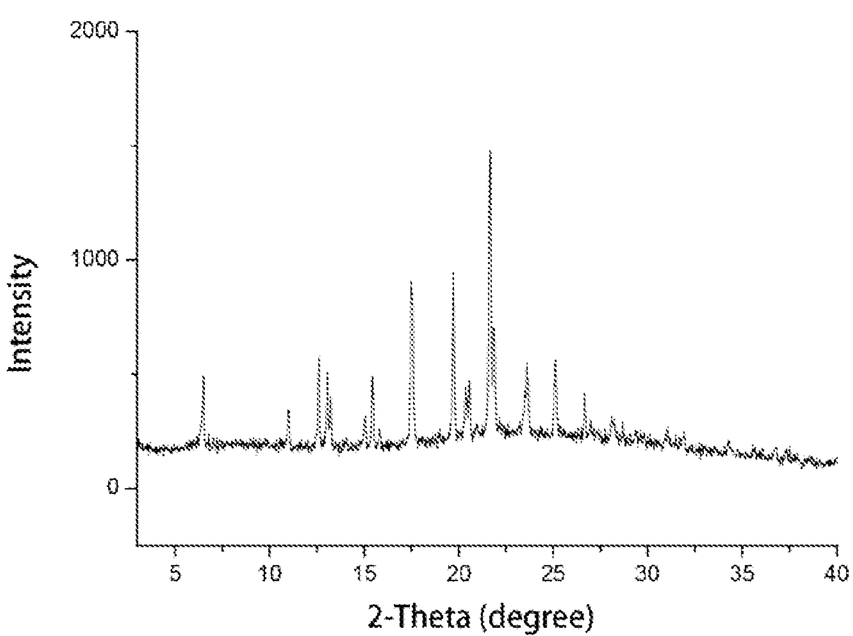
FIG. 7 is the X-ray powder diffraction (XRPD) pattern of Composition 4.
Figure 8:
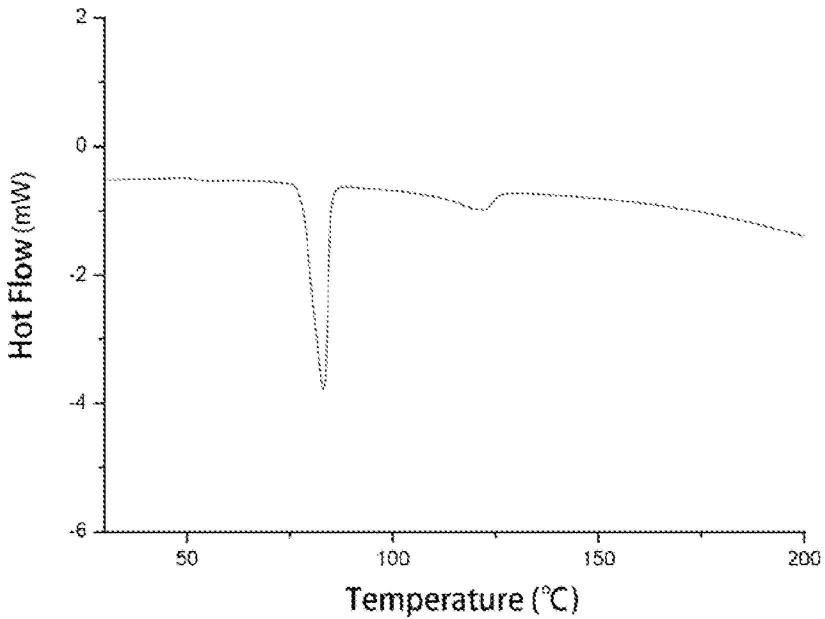
FIG. 8 is the differential scanning calorimetry (DSC) pattern of Composition 4.

The samples prepared in Preparation Example 4 were characterized by X-ray powder diffraction (XRPD) and differential scanning calorimetry (DSC) methods. The results of the samples obtained in the above three preparation processes were consistent, as shown in FIGS. 7 and 8. FIG. 7 is the X-ray powder diffraction (XRPD) pattern of Composition 4; and FIG. 8 is the differential scanning calorimetry (DSC) pattern of Composition 4.

Preparation Example 5: Preparation of Composition 5

The preparation process of composition 5 was as follows.

5 mmol of thymol, 5 mmol of carvacrol and 10 mmol of L-proline were added to a ball mill at a molar ratio of 1:1:2 and vibrated at a vibrating frequency of 30 Hz for a vibrating time of 20 minutes to obtain Composition 5, which was a crystalline powder with good fluidity, with a yield of 98%.

Alternatively, 5 mmol of thymol, 5 mmol of carvacrol and 10 mmol of L-proline were added to a pulverizer at a molar ratio of 1:1:2 and pulverized for 2 minutes to obtain Composition 5, which was a crystalline powder with good fluidity, with a yield of 95%.

Figure 9:
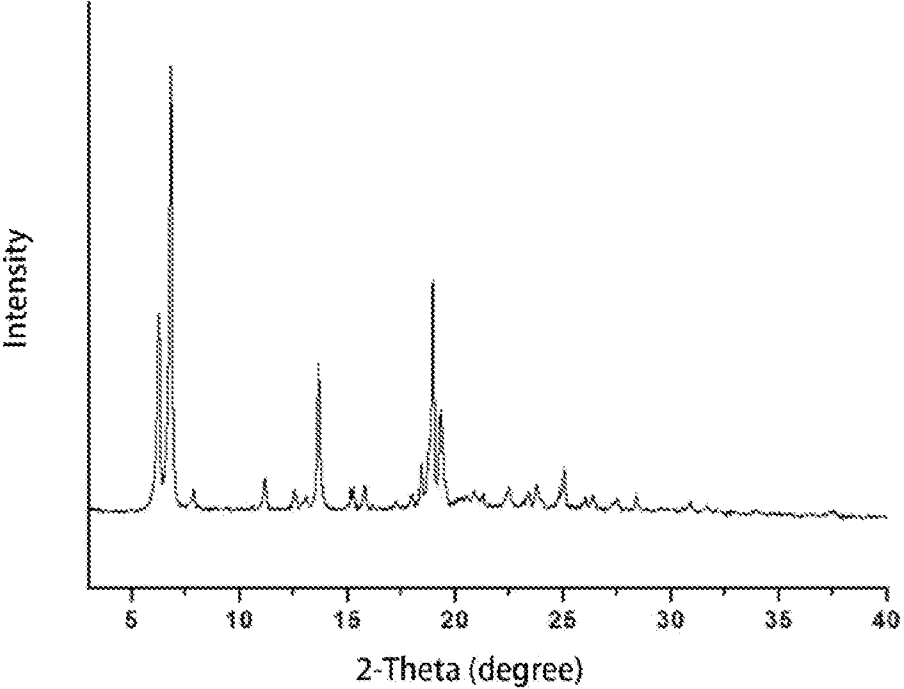
FIG. 9 is the X-ray powder diffraction (XRPD) pattern of Composition 5.
Figure 10:
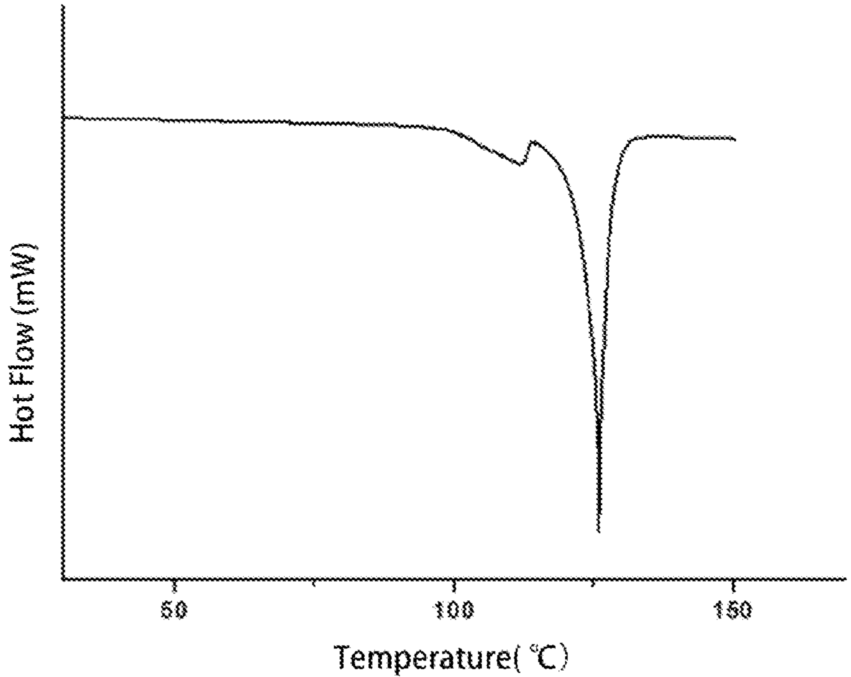
FIG. 10 is the differential scanning calorimetry (DSC) pattern of Composition 5.

The samples prepared in Preparation Example 5 were characterized by X-ray powder diffraction (XRPD) and differential scanning calorimetry (DSC) methods. The results of the samples obtained in the above two preparation processes were consistent, as shown in FIGS. 9 and 10. FIG. 9 is the X-ray powder diffraction (XRPD) pattern of Composition 5; and FIG. 10 is the differential scanning calorimetry (DSC) pattern of Composition 5.

TEST EXAMPLES

Test Example 1

The melting points of Composition 1, Composition 2, Composition 3 and Composition 4 were obtained from the DSC patterns, and the results were shown in the table below.

TABLE 1

| Sample | Thymol | Carvacrol | Composition 1 | Composition 2 | Composition 3 | Composition 4 |
|---|---|---|---|---|---|---|
| Melting point (° C.) | 50 | 2 | 129 | 123 | 133 | 80 |

Test Example 2

Thymol and/or carvacrol and L-proline and/or sarcosine were added to a ball mill according to the compositions shown in Table 2, and vibrated at a vibrating frequency of 30 Hz for a vibrating time of 20 minutes to obtain the compositions. The compositions were subjected to thermogravimetric analysis (TGA), kept at 80° C. for 100 minutes, and the vapor pressure of thymol and/or carvacrol and the compositions thereof were calculated according to the formula:

$$p = \alpha^{-1}(-dm/dt)(2\pi RT/M)^{1/2}$$

wherein m is the mass of the sample at time t, −dm/dt is the weight loss rate per unit area, p is the saturated vapor pressure, α is the vaporization constant, T is the absolute temperature, R is the gas constant, and M is the molecule mass of the evaporated substance. Under vacuum condition, α=1. α can be considered as a constant when a protective gas is present.

The greater the vapor pressure, the stronger the volatility. It can be seen from Table 2 that the vapor pressure was significantly reduced after formation of the compositions. Therefore, the volatility could be effectively reduced, thereby significantly improving the stability during processing and storage. The compositions of the invention significantly reduced the vapor pressures of thymol and carvacrol, so that the volatilization was reduced and the stability was improved. It can be seen that the compositions of thymol and/or carvacrol and sarcosine and/or proline can significantly reduce the vapor pressures of thymol and/or carvacrol, so that the volatilization was reduced and the stability was improved.

TABLE 2

Compositions and vapor pressures (interaction at molecular level is present between thymol or carvacrol and the amino acid in the compositions)

| | Composition (molar ratio) | vapor pressure (Pa) at 80° C. |
|---|---|---|
| | thymol | 333 |
| | carvacrol | 242 |
| Composition 1 | thymol and sarcosine 1:2 | 35 |
| Composition 2 | thymol and L-proline 1:1 | 43 |
| Composition 3 | carvacrol and L-proline 1:1 | 21 |
| Composition 4 | carvacrol and L-proline 2:1 | 163 |
| Composition 5 | thymol-carvacrol-proline1:1:2 | 30 |
| Composition 6 | thymol-carvacrol-sarcosine 1:1:2 | 36 |
| Composition 7 | thymol-proline 2:1 | 169 |
| Composition 8 | thymol-proline 1:2 | 84 |
| Composition 9 | carvacrol-proline 1:2 | 40 |
| Composition 10 | thymol-sarcosine 2:1 | 263 |
| Composition 11 | thymol-sarcosine 1:3 | 66 |
| Composition 12 | carvacrol-sarcosine 1:2 | 188 |
| Composition 13 | thymol-sarcosine 1:9 | 39 |
| Composition 14 | thymol-sarcosine 9:1 | 81 |
| Composition 15 | thymol-proline 1:9 | 46 |
| Composition 16 | thymol-proline 9:1 | 97 |
| Composition 17 | carvacrol-proline 1:9 | 27 |
| Composition 18 | thymol-carvacrol-proline 1:1:18 | 42 |

Test Example 3

This experiment adopted a single factor design, and 4 treatments were set up: Treatment 1: no essential oil was added to the basal diet; Treatment 2: 30 mg/kg of Composition 5 was added to the basal diet; Treatment 3: 60 mg/kg of Composition 5 was added to the basal diet; Treatment 4:120 mg/kg of Composition 5 was added to the basal diet.

384 1-day-old meat ducks were divided into 4 treatment groups, each treatment had 6 replicates, and each replicate had 16 ducks; the basal diet was corn soybean meal; the test period was 35 days, which was divided into two stages of 1-14 day-old and 15-35 day-old for feeding.

As shown in Table 3, compared with the treatment 1 wherein the plant essential oil composition was not added, the death rate was significantly reduced in the treatments 2-3, and the death rate was 0 when the addition amount reached 120 mg/kg. It can be seen that the advantages of using the composition provided by the present invention as animal feed additives are that the Composition provided by the present invention is less volatile, has better palatability and improved stability, and fully exerts antibacterial properties in animals and reduces the death rate while maintaining quality and quantity. It can be shown from the test results in meat ducks that the composition provided by the present invention has the effect of significantly reducing the death rate.

TABLE 3

Test results in meat ducks

| Item | Treatment 1 | Treatment 2 | Treatment 3 | Treatment 4 |
|---|---|---|---|---|
| Death rate for 1-35 days | 8.3% | 7.3% | 4.2% | 0% |

Test Example 4

The accelerated stability advantage of Composition 5 was examined.

The sources of the tested samples: the sample of Composition 5 prepared in Preparation Example 5 above and the commercially available mixed essential oil additive coating product A (containing 25% thymol and 25% carvacrol).

Under the condition of 40° C./75% RH, the contents of thymol and carvacrol in Composition 5 were 25.7%/25.5% respectively at day 0, and the contents of thymol and carvacrol in the additive product A were 26.1%/26.2% respectively. After 2 months, the contents of thymol and carvacrol in Composition 5 were 25.6%/25.2%, respectively, and the contents of thymol and carvacrol in the additive product A were 20.6%/20.7%, respectively.

After 2 months of accelerated testing, the retention rate was 99.2% for Composition 5, while both thymol and carvacrol in the product A were unstable, with a retention rate of 79.0%, indicating that the composition of the present invention had better storage stability.

TABLE 4

| Comparison of storage stability with the commercially available product A | | | | | | |
|---|---|---|---|---|---|---|
| | Day 0 | | One month | | Two months | |
| 40° C./75% RH | thymol | carvacrol | thymol | carvacrol | thymol | carvacrol |
| Composition 5 | 25.7% | 25.5% | 25.9% | 25.1% | 25.6% | 25.2% |
| Product A | 26.1% | 26.2% | 21.3% | 21.3% | 20.6% | 20.7% |

Test Example 5

The stability advantage of Composition 5 during granulation was examined.

Sources of the tested samples: the sample of Composition 5 prepared in Preparation Example 5 above and the commercially available mixed essential oil additive product B (containing 8.5% thymol and 8.5% carvacrol).

Granulation processing was performed referring to the meat duck feed of the Chinese duck feeding standard, and the retention rate of the essential oil was 53% for the product B, while the retention rate was 72.3% for Composition 5. It can be seen that the essential oil in the composition of the present invention had better processing stability.

TABLE 5

| Comparison of retention rate with commercially available product B after granulation | | |
|---|---|---|
| Group | Composition 5 | Product B |
| Theoretical added value (thymol + carvacrol, ppm) | 60 | 34 |
| Measured value in feed (thymol + carvacrol, ppm) | 43.4 | 18.1 |
| Retention rate of essential oil in feed | 72.3% | 53% |

Test Example 6

This experiment adopted a single factor design, and 4 treatments were set up: Treatment 1: no essential oil was added to the basal diet; Treatment 2: 30 mg/kg of Composition 5 was added to the basal diet; Treatment 3: 60 mg/kg of Composition 5 was added to the basal diet; Treatment 4:120 mg/kg of Composition 5 was added to the basal diet.

640 1-day-old broilers were divided into 4 treatment groups, each treatment had 8 replicates, and each replicate had 20 broilers; the basal diet was corn soybean meal; the test period was 42 days, which was divided into two stages of 1-21 day-old and 22-42 day-old for feeding.

As shown in Table 6, compared with the treatment 1 wherein the plant essential oil composition was not added, the body weights were significantly increased in the treatments 2-4, and the body weight was increased by 6% when the addition amount was 30 mg/kg. It can be seen that the advantages of using the composition provided by the present invention as an animal feed additive are that the composition provided by the present invention is less volatile, has better palatability and improved stability, and fully exerts antibacterial properties in animals and reduces the death rate while maintaining quality and quantity. It can be shown from the test results in broilers that it has the effect of significantly increasing the body weight.

TABLE 6

| test results in broilers | | | | | | |
|---|---|---|---|---|---|---|
| Item | Treatment 1 | Treatment 2 | Treatment 3 | Treatment 4 | SEM | P |
| Average weight on day 1 (g) | 43.05 | 43.15 | 43.08 | 42.98 | 0.09 | 0.321 |
| Average weight on day 42 (g) | $2704.66^{b}$ | $2866.82^{a}$ | $2809.22^{a}$ | $2856.01^{a}$ | 49.56 | 0.026 |
| Average daily weight gain for 1-42 days (g) | $63.37^{b}$ | $67.23^{a}$ | $65.86^{a}$ | $66.98^{a}$ | 1.18 | 0.026 |
| Average feed intake (g) | 116.52 | 120.67 | 119.37 | 119.16 | 2.20 | 0.354 |
| Feed conversion ratio for 1-42 days | 1.84 | 1.80 | 1.81 | 1.78 | 0.02 | 0.029 |

For the data in the same row, different lowercase letters on the shoulders indicate significant differences ($p < 0.05$), and the same or no letters indicate no significant differences ($p > 0.05$).

Test Example 7

This experiment adopted a single factor design, and 4 treatments were set up: Treatment 1: no essential oil was added to the basal diet; Treatment 2: 30 mg/kg composition 5 was added to the basal diet; Treatment 3: 60 mg/kg Composition 5 was added to the basal diet; Treatment 4:120 mg/kg composition 5 was added to the basal diet.

For a 28-day feeding experiment, 96 weaned piglets were divided into 4 treatment groups, each treatment had 4 replicates, and each replicate had 6 piglets; the body weight, feed intake, and daily diarrhea situation were recorded for each replicate at day 1 and 28 respectively, and feed conversion ratio and diarrhea rate were calculated.

As shown in Table 7, compared with Treatment 1 wherein the plant essential oil composition was not added, when the test was ended on day 28, in the treatment group 3 wherein the addition amount was 60 mg/kg, the body weight was significantly increased, the feed conversion ratio was significantly decreased, and the body weight was increased by 15%, and the feed conversion ratio was reduced by 22%.

TABLE 7

Experimental results in weaned piglets

| Item | Treatment 1 | Treatment 2 | Treatment 3 | Treatment 4 | SEM | P |
|---|---|---|---|---|---|---|
| Body weight/kg | | | | | | |
| Day 1 | 7.90 | 7.88 | 7.88 | 7.93 | 0.2 | 0.998 |
| Day 28 | $13.27^{b}$ | $14.40^{ab}$ | $15.63^{a}$ | $13.85^{ab}$ | 0.67 | 0.118 |
| Average daily feed intake ADFI/(g/d) | | | | | | |
| Days 1-28 | 391 | 413 | 428 | 361 | 0.04 | 0.647 |
| Average daily weight gain ADG/(g/d) | | | | | | |
| Days 1-28 | 179 | 213 | 263 | 198 | 35 | 0.399 |
| Feed conversion ratio F/G | | | | | | |
| Days 1-28 | $2.19^{a}$ | $2.01^{ab}$ | $1.71^{b}$ | $1.85^{ab}$ | 0.14 | 0.14 |

For the data in the same row, different lowercase letters on the shoulders indicate significant differences ($p < 0.05$), and the same or no letters indicate no significant differences ($p > 0.05$).

The above description are only specific embodiments of the present invention, but the protection scope of the present invention is not limited thereto, any changes or substitutions that can be conceived by those skilled in the art within the technical scope disclosed in the present invention without creative efforts shall be covered by the protection scope of the present invention.

What is claimed is:

1. A composition comprising a plant essential oil and an amino acid, the composition is obtained by mixing a plant essential oil with an amino acid, the plant essential oil is one or two selected from the group consisting of thymol and carvacrol, the amino acid is one or two selected from the group consisting of L-proline and sarcosine, wherein the composition is selected from the group consisting of composition 1, composition 2, composition 3, composition 4, and composition 5, wherein:

the composition 1 is obtained by mixing thymol with sarcosine at a molar ratio of 1:2, and has an X-ray powder diffraction pattern showing characteristic peaks at 2θ angles of 6.4°±0.2°, 12.1°±0.2°, 12.4°±0.2°, 17.7°±0.2°, 20.2°±0.2°, 22.1°±0.2°, 23.0°=0.2°, 23.7°±0.2° and 25.1°±0.2°, the composition 2 is obtained by mixing thymol with L-proline at a molar ratio of 1:1, and has an X-ray powder diffraction pattern showing characteristic peaks at 2θ angles of 6.2°±0.2°, 6.9°±0.2°, 12.5°±0.2°, 13.8°±0.2°, 18.0°±0.2°, 18.4°±0.2°, 18.7°±0.2°, 19.1°±0.2°, 19.3°±0.2°, 21.1°±0.2° and 24.8°±0.2°, the composition 3 is obtained by mixing carvacrol with L-proline at molar ratio of 1:1, and has an X-ray powder diffraction pattern showing characteristic peaks at 2θ angles of 6.9°±0.2°, 11.5°±0.2°, 13.6°±0.2°, 13.9°±0.2°, 19.0°±0.2°, 19.2°±0.2°, 23.1°±0.2° and 24.9°±0.2°, the composition 4 is obtained by mixing carvacrol with L-proline at a molar ratio of 2:1, and has an X-ray powder diffraction pattern showing characteristic peaks at 2θ angles of about 6.5°±0.2°, 11.0°±0.2°, 13.1°±0.2°, 13.2°±0.2°, 15.0°±0.2°, 15.5°±0.2°, 15.8°±0.2°, 17.5°±0.2°, 19.7°±0.2°, 20.5°±0.2°, 21.6°±0.2°, 21.9°±0.2°, 23.6°±0.2°, 25.1°±0.2° and 26.7°±0.2°, and the composition 5 is obtained by mixing thymol, carvacrol and L-proline at a molar ratio of 1:1:2, and has an X-ray powder diffraction pattern showing characteristic peaks at 2θ angles of about 6.2°±0.2°, 6.8°±0.2°, 12.5°±0.2°, 13.8°±0.2°, 18.4°±0.2°, 18.8°±0.2°, 19.4°±0.2°, 21.3°±0.2°, 24.8°±0.2° and 25.0°±0.2°.

2. A product comprising the composition according to claim 1, wherein the product is at least one of a health product, a food, a cosmetic, a medicine, a pharmaceutical excipient, or a feed.

3. A method for preparing the composition according to claim 1, comprising a step of mixing the plant essential oil with the amino acid to obtain a composition comprising the plant essential oil and the amino acid.

4. The method according to claim 3, wherein the mixing comprises one of the following methods (1) and (2):

Method (1): the plant essential oil and the amino acid are recrystallized in a solvent to obtain a precipitate, and the precipitate is dried to obtain a composition comprising the plant essential oil and the amino acid; and Method (2): the plant essential oil and the amino acid are mixed to obtain a mixture, and the mixture is added to a crushing equipment to make them fully contact by mechanical force, or a solution of the mixture is subjected to spray-drying, or the mixture is treated with an extruder, and after partial or complete reaction, a composition comprising the plant essential oil and the amino acid is formed, wherein the crushing equipment is selected from the group consisting of a ball mill, a pulverizer, a mixer and a stirring device.

* * * * *